US009371586B2

(12) United States Patent
Zielecka et al.

(10) Patent No.: US 9,371,586 B2
(45) Date of Patent: Jun. 21, 2016

(54) METHOD OF MANUFACTURING THE SILICA NANOPOWDERS WITH BIOCIDAL PROPERTIES, ESPECIALLY FOR POLYMER COMPOSITES

(75) Inventors: Maria Zielecka, Warsaw (PL); Elżbieta Bujnowska, Warsaw (PL); Magdalena Wenda, Radom (PL); Regina Jeziórska, Warsaw (PL); Krystyna Cyruchin, Warsaw (PL); Anna Pytel, Warsaw (PL); Blanka Kepska, Mińsk Mazowiecki (PL)

(73) Assignee: INSTYTUT CHEMII PRZEMYSLOWEJ IM. PROF IGNACEGO MOSCICKEIGO, Warszawa (PL)

( * ) Notice: Subject to any disclaimer, the term of this patent is extended or adjusted under 35 U.S.C. 154(b) by 0 days.

(21) Appl. No.: 13/574,922

(22) PCT Filed: Jan. 21, 2011

(86) PCT No.: PCT/PL2011/000008
§ 371 (c)(1),
(2), (4) Date: Jul. 24, 2012

(87) PCT Pub. No.: WO2011/093731
PCT Pub. Date: Aug. 4, 2011

(65) Prior Publication Data
US 2012/0308666 A1    Dec. 6, 2012

(30) Foreign Application Priority Data
Jan. 27, 2010    (PL) .......................................... 390296

(51) Int. Cl.
| B60C 1/00 | (2006.01) |
| C23C 18/08 | (2006.01) |
| A01N 59/16 | (2006.01) |
| B82Y 30/00 | (2011.01) |
| C09C 1/00 | (2006.01) |
| C09C 1/30 | (2006.01) |

(52) U.S. Cl.
CPC ................ *C23C 18/08* (2013.01); *A01N 59/16* (2013.01); *B82Y 30/00* (2013.01); *C09C 1/0081* (2013.01); *C09C 1/3045* (2013.01); *C01P 2004/62* (2013.01)

(58) Field of Classification Search
None
See application file for complete search history.

(56) References Cited

U.S. PATENT DOCUMENTS

| 4,122,158 A * | 10/1978 | Schmitt .......................... 424/444 |
| 2007/0167554 A1 * | 7/2007 | Ryang ............................ 524/492 |
| 2009/0149426 A1 | 6/2009 | Lee et al. |

FOREIGN PATENT DOCUMENTS

DE    102008013143 A1    9/2009

OTHER PUBLICATIONS

Flores, J.C., et al., "Preparation of core-shell nanospheres of silica-silver: SiO2©Ag", Journal of Non-Crystalline Solids, North-Holland Physics Publishing, Amsterdam, NL, vol. 354, No. 52-54, Dec. 15, 2008, pp. 5435-5439.
Shibata, S., et al., "Preparation of Silica Microspheres Containing Ag Nanoparticles", Journal of Sol-Gel Science and Technology, Aug. 1998, Kluwer Academic Publishers NL, vol. 11, No. 3, pp. 279-287.
Jasiorski, M. et al., "Surface-enhanced Raman spectra of substances adsorbed on Ag,<0> clusters deposited on Si02 submicron spheres prepared by the sol-gel method", Optical Materials, Elsevier Science Publishers B.V. Amsterdam, NL, vol. 26, No. 2, Jul. 1, 2004, pp. 145-149.
Angelito-Banos, J., et al., "Structural Characterization of Silver Doped Silica Prepared by Two Different Wet Chemical Methods", Journal of Sol-Gel Science and Technology, May 2004, Kluwer Academic Publishers NL, vol. 30, No. 2, May 2004, pp. 89-94.
Huang, Chih-Kai, et al., "Immobilization of silver nanoparticles on silica microspheres", Journal of Nanoparticle Research; An Interdisciplinary Forum for Nanoscale Science and Technology, Kluwer Academic Publishers, DO, vol. 12, No. 1, Feb. 19, 2009, pp. 199-207.
International Search Report issued in PCT/PL2011/000008 dated Apr. 29, 2011.

* cited by examiner

*Primary Examiner* — Nannette Holloman
(74) *Attorney, Agent, or Firm* — Hoffmann & Baron, LLP

(57) ABSTRACT

Silica nanopowders with biocidal properties, especially for polymer composites, are produced by sol-gel method. The silica sol is produced from the aqueous mixture containing tetraalkoxysilane, in which alkoxy group contains from $C_1$ to $C_4$ carbon atoms, an alcohol or the mixture of aliphatic alcohols from $C_1$ to $C_4$, in the mole ratio of 1:5 to 1:35, in the presence of ammonium compound, used in an amount of from 0.001 to 0.05 mol per 1 mol of tetraalkoxysilane, with introducing, after thorough mixing of components, the silver salt in the form of aqueous solution in an amount from 0.02 to 1 mol per 1 mol of tetraalkoxysilane, and subsequently the aqueous solution of alkali metal hydroxide in an amount from 0.02 to 1 mol of hydroxide per 1 mol of tetraalkoxysilane.

9 Claims, No Drawings

METHOD OF MANUFACTURING THE SILICA NANOPOWDERS WITH BIOCIDAL PROPERTIES, ESPECIALLY FOR POLYMER COMPOSITES

CROSS-REFERENCE TO RELATED APPLICATIONS

This application is a National Phase application of International Application No. PCT/PL2011/000008 filed Jan. 21, 2011 which claims priority to Polish Patent Application No. P-390296 filed Jan. 27, 2010, the disclosures of which are incorporated herein by reference.

BACKGROUND

The invention relates to a method of manufacturing the silica nanopowders with biocidal properties, especially for polymer composites.

The high requirements for materials used in such fields as medicine (equipment, room equipment, protective clothing, prostheses), textile and footwear industry, household goods, plastics, paints, lacquers, are the reason of the intensification of research on obtaining the high molecular mixtures having bactericidal and/or fungicidal properties.

From the scientific literature there is known the use of colloidal silver solutions as a biocide additive for different materials such as plastics, coated fabrics etc. It was found that biocidal properties of colloidal silver solutions occur already at the concentration of 1 ppm (Gaisford S., Blezer A. E., Bishop A. H., Walter M., Parsons D. International Journal of Pharmaceutics 2009, 366, 11-116). In several publication the authors stress that the problem occurring in the use of colloidal silver is the agglomeration of silver particles and their coagulation, hampering to a large extend obtaining the required biocidal activity (Halbig P., Gran H., Nickel U. Photochem. Photo-biol. 1994, 60 , 605; Schktcliff N., Nickel U., Schneider S., J. Colloid Interface Sci. 1999, 211, 122; Rivas I., Sanchez-Cortes S., Garcia-Ramos J. V., Morcillo G., Langmuir 2001, 17, 574; Nickel U., Castell A Z., Poppl K., Schneider S., Langmuir 2000, 16, 9087). Silver nanoparticles have significantly higher biocidal activity than silver microparticles. The achievement of biocidal activity in the case of silver microparticles requires the use of concentration $10^3$ higher than in the case of the concentration of silver nanoparticles to obtain the acceptable biocidal activity (Damm C., Munstedt H., Rosch A., Materials Chemistry and Physics 2008, 108, 61-66).

Sharma V. K., Yngard R A., Lin Y., Advances in Colloidal and Interface Sci 2009, 145, 83, described the studies on the methods of the stabilization of colloidal silver particles with the use of protective colloids or by fixation in polymer particles. The use of such stabilized silver colloids is limited due to the unfavorable effect of stabilizers on the properties of obtained material.

From patent specifications U.S. Pat. No. 6,482,444, U.S. Pat. No. 6,495,257 and US 2006/0246149 there also known powders, comprising of particles, e.g. $SiO_2$, comprising microparticles of metal compounds, i.a. zinc oxide, silver oxide. These powders characterize with higher grain sizes (than nanoparticles), and in that the microparticles of metal compounds are inside the particles.

There is known a process of manufacturing, by sol-gel method, of spherical $SiO_2$ particles, containing inclusions nanometric silver particles, described and Polish Patent application P-360190. The sizes of silica powder grains is in the range of 200 to 800 nm. However it is not possible to obtain with that method the silica nanopowders of the sizes below 200 nm, containing nanoparticles of metallic silver. It is a significant limitation in their use as nanofillers of polymer composites.

The unique properties of polymeric nanocomposites are connected with small dimensions of nanofiller particles and they differ distinctly from the properties of composites obtained from particles above 200 nm. Nanocomposites obtained just from some percent contents of nanofillers (0.5-5%) show specifically preferred properties, i.a. improved barrier properties as well as much higher mechanical and optical properties, better thermal and chemical resistance, reduced flammability and smaller coefficient of linear expansion. To obtain the similar effect with the use of conventional fillers it is necessary to use them in significant amount (from 10 to several dozen percents).

From the patent specification PL 198 188 there is known a process of manufacturing, by sol-gel method, of silica nanopowders with small polydispersity of particle size, including functionalized ones. The size of silica nanopowder obtained with the described process depends on the amount of used catalyst and the composition of the reaction mixture. The polymeric nanocomposites obtained with the use of such nanopowder show very good physico-mechanical properties, especially with the use of functionalized nanopowder, durably embedded in the polymer matrix.

SUMMARY

The instant invention solves the problem of manufacturing the silica nanopowders with biocidal properties, containing immobilized nanometric silver particles, obtained by "in situ" method. Silver nanoparticles incorporated into silica structure are stabile and do not coagulate during storage, assuring the stability of biocidal properties and solving the problem of the decay of such properties due to the agglomeration of silver particles. The silica nanopowder obtained by the method of the invention, with immobilized silver nanoparticles are characterized with good repeatability of physicochemical properties, small particle size distribution, uniform distribution of silver nanoparticles on silica nanoparticles, confirmed by scanning electron microscopy.

DETAILED DESCRIPTION

The method according to the invention of manufacturing the silica nanopowders with biocidal properties, especially for polymer composites, by sol-gel method, is characterized in that, the silica sol is obtained from the aqueous mixture containing tetraalkoxysilane, in which alkoxy group contains from $C_1$ to $C_4$ carbon atoms, an alcohol or the mixture of aliphatic alcohols from $C_1$ to $C_4$, in the mole ratio of 1:5 to 1:35, respectively, in the presence of ammonium compound, used in an amount of from 0.001 to 0.05 mol per 1 mol of tetraalkoxysilane, with introducing, after thorough mixing of components, the silver salt in the form of aqueous solution in an amount from 0.02 to 1 mol per 1 mol of tetraalkoxysilane, and subsequently the aqueous solution of alkali metal hydroxide in an amount from 0.02 to 1 mol of hydroxide per 1 mol of tetraalkoxysilane.

Preferably, tetramethylammonium hydroxide or tetraethylammonium hydroxide is used as an ammonium compound.

Preferably, silver nitrate is used as a silver salt.

Preferably, sodium hydroxide is used as an alkali metal hydroxide.

Silica nanopowders containing immobilized silver nanoparticles, obtained by the method of invention are separated by solvent evaporation and drying the residue. Drying time is depended on the temperature, which generally does not exceed 250° C.

Silica nanopowders containing immobilized silver nanoparticles, obtained by the method of invention, are stable during storage, and the sizes of nanometric silver particles do not change during prolonged storage.

The properties of immobilized nanometric silver particle containing silica nanopowders obtained by the method of invention, are of great importance in the use of such powders as components of polymer composites, used in the production of elements of moldings with biocidal properties for domestic appliances (refrigerators, washing machines, etc.) as well as the equipment of medical and public utilities, with higher hygiene requirements. The polymer composites as well as blends containing nonwoven fabrics (e.g. cellulose) can be used in the production of packaging materials. Moreover, silica nanopowders, containing immobilized nanometric silver particles, can be used as components of paints designated for painting of compartments with higher hygienic requirements.

The manufacturing of silica nanopowders by the method of the invention is illustrated in the following examples.

EXAMPLE I

In an Erlenmeyer flask there were mixed with the use of magnetic stirrer 89.0 g (1.93 mol) of anhydrous ethanol, 0.09 g (0.001 mol) of 20% aqueous solution of tetramethylammonium hydroxide and 34.2 g (1.9 mol) of distilled water. The pH value of obtained mixture was 11.53. Subsequently, 17.2 g (0.08 mol) of tetraethoxysilane was added to the reaction mixture. The reaction mixture was clear in the initial stage, but after 15 minutes the opalescence of solution was observed. Contents of the flask was maintained at an ambient temperature and was the stirred by 2.5 h. Thereafter, 18 ml of 0.1M aqueous solution of silver nitrate (0.0018 mol, 0.31 g) and 18 ml of 0.1M aqueous solution of sodium hydroxide (0.0018 mol, 0.07 g) were added to the reaction mixture. As a result of the reduction of silver salt the color of reaction mixture was pale gray. The contents of the flask was stirred for 1 h. The analysis of obtained sol by photon correlation spectroscopy showed that the particle size of the sol was 120-132 nm. Thereafter the sample of sol was dried in an oven at the temperature of 90° C. for 1.5 h and at 250° C. for 2 h. A pale gray flowable silica nanopowder was obtained. The particle size of obtained nanopowder was analyzed by scanning electron microscopy and found to be 118-132 nm. The size of immobilized silver particles was 28-57 nm. The contents of silver in a sample was analyzed by EDS X-ray spectroscopy and by atomic absorption spectrometry, and it was found to be 0.004% by weight.

The obtained silica nanopowder—containing immobilized nanometric silver particles was incorporated in an amount of 4.5% by weight to the polymer composite based on polyamide 66. On the basis of performed microbiological tests it was found that the obtained polymer composite containing 0.00018% by weight (1.8 ppm) of silver nanoparticles immobilized on silica nanopowder had a biocidal activity against bacteria *Escherichia coli*.

EXAMPLE II

In an Erlenmeyer flask there were mixed with the use of magnetic stirrer 179.86 g (3.91 mol) of anhydrous ethanol, 0.5 g (0.005 mol) 20% of aqueous tetramethylammonium hydroxide solution and 54.18 g (3.01 mol) of distilled water. The pH value of obtained mixture was =11.59. Subsequently, 29.17 g (0.14 mol) tetraethoxysilane was added to the reaction mixture. The reaction mixture was clear in the initial stage, but after 10 minutes the opalescence of solution was observed. Thereafter, 0.83 g (0.005 mol) of 0.1 M aqueous solution of silver acetate and 0.28 g (0.005 mol) of 0.1 M aqueous solution of potassium hydroxide were added to the reaction mixture. As a result of the reduction with potassium hydroxide the color of reaction mixture was gray. The contents of the flask was kept at an ambient temperature and stirred for 3.5 h. The analysis of obtained sol by photon correlation spectroscopy showed that the particle size of the sol was 178-180 nm. Thereafter the sample of sol was dried in an oven at the temperature of 90° C. for 1.5 h and at 250° C. for 2 h. The brown, flowable silica nanopowder was obtained. The particle size of obtained nanopowder was analyzed by scanning electron microscopy and found to be 180-182 nm. The size of immobilized silver particles was 36-54 nm. The contents of silver in a sample was analyzed by atomic absorption spectrometry, and it was found to be 0.007% by weight.

The obtained silica nanopowder containing immobilized nanometric silver particles was incorporated in an amount of 3% by weight to the polymer composite based on polypropylene. On the basis of performed microbiological tests it was found that the obtained polymer composite containing 0.00021% by weight (2.1 ppm) of silver nanoparticles immobilized on silica nanopowder had a biocidal activity against bacteria *Staphylococcus aureus*.

EXAMPLE III

In an Erlenmeyer flask there were mixed with the use of magnetic stirrer 156.0 g (3.39 mol) of anhydrous ethanol, 1.0 g (0.06 mol) 25% aqueous ammonia and 55.2 g (3.07 mol) of distilled water. The pH value of obtained mixture was =11.4. Subsequently, 20.0 g (0.1 mol) tetraethoxysilane was added to the reaction mixture. The reaction mixture was clear in the initial stage, but after 20 minutes the opalescence of solution was observed. The contents of the flask was kept at an ambient temperature and than stirred for 2.5 h. The analysis of obtained sol by photon correlation spectroscopy showed that the particle size of the sol was 82-85 nm. Thereafter 350 ml of 0.1M aqueous solution of silver nitrate (0.04 mol, 6.8 g) and 350 ml 0.1M aqueous solution of sodium hydroxide (0.04 mol, 1.4 g) were added to the reaction mixture. As a result of the reduction of silver salt the color of reaction mixture was brown. The whole mixture was stirred for 1 h. Thereafter the sample was dried in an oven at the temperature of 90° C. for 1.5 h and at 250° C. for 2 h. The contents of silver in a sample was analyzed by atomic absorption spectrometry, and it was found to be 3.5%. The obtained silica nanopowder containing immobilized nanometric silver particles was incorporated in an amount of 0.25% by weight to the polymer composite based on polyethylene. On the basis of performed microbiological tests it was found that the obtained polymer composite containing 0.00875% by weight (87.5 ppm) of silver nanoparticles immobilized on silica nanopowder had a biocidal activity against bacteria *Staphylococcus aureus* and *Escherichia coli*.

EXAMPLE IV

In an Erlenmeyer flask there were mixed with the use of magnetic stirrer 99.0 g (2.15 mol) of anhydrous ethanol, 1.20 g (0.07 mol), 25% aqueous ammonia and 36.8 g (2.04 mol) of distilled water. The pH value of obtained mixture was =11.5. Subsequently, 19.3 g (0.09 mol) tetraethoxysilane was added to the reaction mixture. The reaction mixture was clear in the initial stage, but after 8 minutes the opalescence of solution was observed. The contents of the flask was kept at an ambient temperature and then stirred for 2.5 h. The analysis of obtained sol by photon correlation spectros-copy showed that the particle size of the sol was 120-132 nm. Thereafter 375 ml 0.1 M aqueous solution of silver nitrate (0.04 mol, 6.4 g) and 375 ml 0.1 M aqueous solution of sodium hydroxide (0.04 mol, 1.5 g) were added to the reaction mixture. As a result of the reduction of silver salt the color of reaction mixture was brown. The whole mixture was stirred for 1 h. Thereafter the sample was: dried in an oven at the temperature of 90° C. for 1.5 h. The particle size of obtained nanopowder was analyzed by scanning electron microscopy and it was found to be 118-135 nm. The size of immobilized silver particles was 38-69 nm. The contents of silver in a sample was analyzed by EDS X-ray spectroscopy and it was found to be 3.2%.

The obtained silica nanopowder containing immobilized nanometric silver particles was incorporated in an amount of 0.75% by weight to the polymer composite based on polyethylene terephthalate. On the basis of performed microbiological tests it was found that the obtained polymer composite containing 0.024% by weight (240 ppm) of silver nanoparticles immobilized on silica nanopowder has a biocidal activity against bacteria *Staphylococcus aureus* and *Escherichia coli*.

EXAMPLE V

In an Erlenmeyer flask there were mixed with the use of magnetic stirrer 107.0 g (2.33 mol) of anhydrous ethanol, 0.5 g (0.03 mol) 25% aqueous ammonia and 38.2 g (2.12 mol) of distilled water. The pH value of obtained mixture was =11.38. Subsequently, 23.5 g (0.11 mol) tetraethoxysilane was added to the reaction mixture. The reaction mixture was clear in the initial stage, but after 20 minutes the opalescence of solution was observed. The contents of the flask was kept at an ambient temperature and then stirred for 2.5 h. The analysis of obtained sol by photon correlation spectroscopy showed that the particle size of the sol was 49-53 nm. Thereafter, 400 ml of 0.1 M aqueous solution of silver nitrate (0.04 mol, 6.8 g) and 400 ml 0.1 M aqueous solution sodium hydroxide (0.04 mol, 1.6 g) were added to the reaction mixture. As a result of the reduction of silver salt the color of reaction mixture was brown. The whole mixture was stirred for 1 h. As a result of the reduction with sodium hydroxide the color of reaction mixture was brown. There-after the sample was dried in an oven at the temperature of 90° C. for 1.5 h. The contents of silver in a sample was analyzed by atomic absorption spectrometry and found to be 4.0%.

The obtained silica nanopowder containing immobilized nanometric silver particles was incorporated in an amount of 1.5% by weight to the polymer composite based on polyamide 6. On the basis of performed microbiological tests it was found that the obtained polymer composite containing 0.06% by weight (600 ppm) of silver nanoparticles immobilized on silica nanopowder has a biocidal activity against bacteria *Staphylococcus aureus* and *Escherichia coli*.

What is claimed is:

1. A method of manufacturing silica nanopowders with biocidal properties, by sol-gel method, consisting in that a silica sol is obtained from an aqueous mixture containing tetraalkoxysilane, in which alkoxy group contains from $C_1$ to $C_4$ carbon atoms, an alcohol or a mixture of aliphatic alcohols from $C_1$ to $C_4$ in the presence of an ammonium compound characterized in that after thorough mixing of components, in situ a silver salt in the form of an aqueous solution is introduced in an amount from 0.02 to 1 mol per 1 mol of tetraalkoxysilane, and subsequently an aqueous solution of alkali metal hydroxide in an amount from 0.02 to 1 mol of hydroxide per 1 mol of tetraalkoxysilane.

2. The method of claim 1, characterized in that the ammonium compound is tetramethylammonium hydroxide.

3. The method of claim 1, characterized in that the silver salt is silver nitrate.

4. The method of claim 1, characterized in that the alkali metal hydroxide is sodium hydroxide.

5. A method of manufacturing silica nanopowders with biocidal properties using a sol-gel method, the method consisting of:
    preparing an aqueous mixture containing tetraalkoxysilane, an alcohol or a mixture of aliphatic alcohols from $C_1$ to $C_4$, and an ammonium compound, wherein the alkoxy group of tetraalkoxysilane contains from $C_1$ to $C_4$ carbon atoms;
    adding a silver salt to the aqueous mixture to form a first silica sol, wherein the silver salt is in the form of an aqueous solution in an amount from 0.02 to 1 mol per 1 mol of tetraalkoxysilane;
    adding an aqueous solution of alkali metal hydroxide to the first silica sol to form a second silica sol, wherein the aqueous solution of alkali metal hydroxide is in an amount from 0.02 to 1 mol of hydroxide per 1 mol of tetraalkoxysilane;
    mixing the second silica sol to form a silica gel; and
    drying the silica gel to form a nanopowder containing immobilized silver particles.

6. The method of claim 5, wherein the nanopowder has a particle size of less than 180 nm.

7. The method of claim 5, characterized in that the ammonium compound is tetramethylammonium hydroxide.

8. The method of claim 5, characterized in that the silver salt is silver nitrate.

9. The method of claim 5, characterized in that the alkali metal hydroxide is sodium hydroxide.

* * * * *